United States Patent [19]

Richmond et al.

[11] Patent Number: 4,655,754

[45] Date of Patent: Apr. 7, 1987

[54] VACUUM WOUND DRAINAGE SYSTEM AND LIPIDS BAFFLE THEREFOR

[75] Inventors: James W. Richmond, Kalamazoo; Robert G. Tice, Portage; William M. Booth, III, Paw Paw, all of Mich.

[73] Assignee: Stryker Corporation, Kalamazoo, Mich.

[21] Appl. No.: 670,177

[22] Filed: Nov. 9, 1984

[51] Int. Cl.[4] ............................................. A61M 1/00
[52] U.S. Cl. ..................................... 604/323; 604/126; 210/335; 210/416.1; 210/436; 210/927; 137/197; 137/205
[58] Field of Search .................. 604/317, 319–321, 604/333, 323, 126; 128/760, 762, 766; 137/197, 205; 210/335, 416.1, 433.2, 436, 472, 927

[56] References Cited

U.S. PATENT DOCUMENTS

| Re. 29,321 | 7/1977 | Holbrook | 604/319 |
|---|---|---|---|
| 2,397,257 | 3/1946 | Goland et al. | |
| 3,565,076 | 2/1971 | Kadan | |
| 3,572,340 | 3/1971 | Lloyd et al. | |
| 3,675,653 | 7/1972 | Crowley et al. | |
| 3,719,197 | 3/1973 | Pannier, Jr. et al. | 604/320 |
| 3,768,478 | 10/1973 | Fertik et al. | 604/320 |
| 3,918,453 | 11/1975 | Leonard | |
| 3,955,574 | 5/1976 | Rubinstein | |
| 3,982,538 | 9/1976 | Sharpe | 604/320 |
| 3,993,062 | 11/1976 | Jess | |
| 4,022,209 | 5/1977 | Nehring | |
| 4,073,294 | 2/1978 | Stanley et al. | |
| 4,111,204 | 9/1978 | Hessel | |
| 4,157,967 | 6/1979 | Meyst et al. | 210/927 |
| 4,178,932 | 12/1979 | Ryder et al. | |
| 4,184,510 | 1/1980 | Murry et al. | |
| 4,256,109 | 3/1981 | Nichols | |
| 4,261,360 | 4/1981 | Perez | |
| 4,306,558 | 12/1981 | Kurtz | |
| 4,345,342 | 8/1982 | Saito | |
| 4,392,858 | 7/1983 | George et al. | |
| 4,395,258 | 7/1983 | Wang et al. | |
| 4,401,566 | 8/1983 | Igari et al. | 210/433.2 |
| 4,443,220 | 4/1984 | Haver et al. | 604/319 |
| 4,516,973 | 5/1985 | Telang | 604/319 |

FOREIGN PATENT DOCUMENTS

WO80/02706 12/1980 PCT Int'l Appl. .

OTHER PUBLICATIONS

Copy of Swank article entitled, "Alteration of Blood on Storage: Measurement of Adhesiveness of Aging Platelets and Leukocytes and Their Removal by Filtration", *The New England Journal of Medicine,* vol. 265, No. 15, Oct. 12, 1961, pp. 728–733.

*Primary Examiner*—David L. Lacey
*Attorney, Agent, or Firm*—Flynn, Thiel, Boutell & Tanis

[57] ABSTRACT

Apparatus for selectively blocking passage of lipids in a liquid flow path. A baffle interposed in the liquid flow path is of nonpolar material and is arranged to permit liquid flow therethrough with contact of said liquid with the nonpolar material of the baffle for removing lipids from the flow. In one embodiment, the baffle is interposed between a wound drain connection and vacuum connection in a drain reservoir and protects a hydrophobic filter which is at the end of a vacuum passage communicating with the interior of the drain reservoir. The baffle enables use of a nonpolar material for the hydrophobic filter and avoids coating and thereby clogging of the hydrophobic filter by lipids in the liquid drained from a wound.

18 Claims, 7 Drawing Figures

VACUUM WOUND DRAINAGE SYSTEM AND LIPIDS BAFFLE THEREFOR

FIELD OF THE INVENTION

This invention relates to a vacuum drainage system for wounds, and more particularly to such a system having a reservoir connectable to the wound for receiving drainage liquid therefrom and apparatus for applying a subatmospheric pressure to the reservoir.

BACKGROUND OF THE INVENTION

U.S. patent application Ser. No. 404,791, now U.S. Pat. No. 4,569,674 issued Feb. 11, 1986, assigned to the assignee of the present invention, discloses a wound vacuum drainage system of the above mentioned kind.

While the latter has been found satisfactory in operation, Applicants have been engaged in a continuing effort to improve on systems of this type. Applicants have determined that by installing a hydrophobic filter in the drain reservoir, between the liquid chamber thereof and the vacuum passage, the apparatus of the prior application can be simplified, for example by elimination of a float valve, while protecting the vacuum passage in the drain reservoir and the vacuum pump in the base unit against contamination by wound drainage liquid from the drain reservoir.

However, Applicants have also found that wound drainage liquid often includes lipids (fatty substances) which tend to coat and hence clog the hydrophobic filter and that this may interfere with evacuating the drain reservoir to the desired subatmospheric pressure level, to enable continued vacuum draining of the wound.

Accordingly, the objects and purposes of this invention include provision of:

Apparatus for suction draining of a wound in which a hydrophobic filter is interposed in the connection between the reservoir chamber and the vacuum line to which the suction pump of a base unit are connectable, for preventing contamination of such vacuum passage and suction pump with wound drainage liquid.

An apparatus as aforesaid in which coating and hence clogging of the hydrophobic filter by lipids in the wound drainage liquid is prevented or avoided to increase the useful life span of the drain reservoir by making it possible to repeatedly charge same with vacuum by connection to a base unit.

An apparatus as aforesaid in which protection of the hydrophobic filter is provided at relatively low cost in a relatively simple manner.

Other objects and purposes of the invention will be apparent to persons of ordinary skill in this art by reading the accompanying specification and inspecting the accompanying drawings.

DETAILED DESCRIPTION

Figure 1:
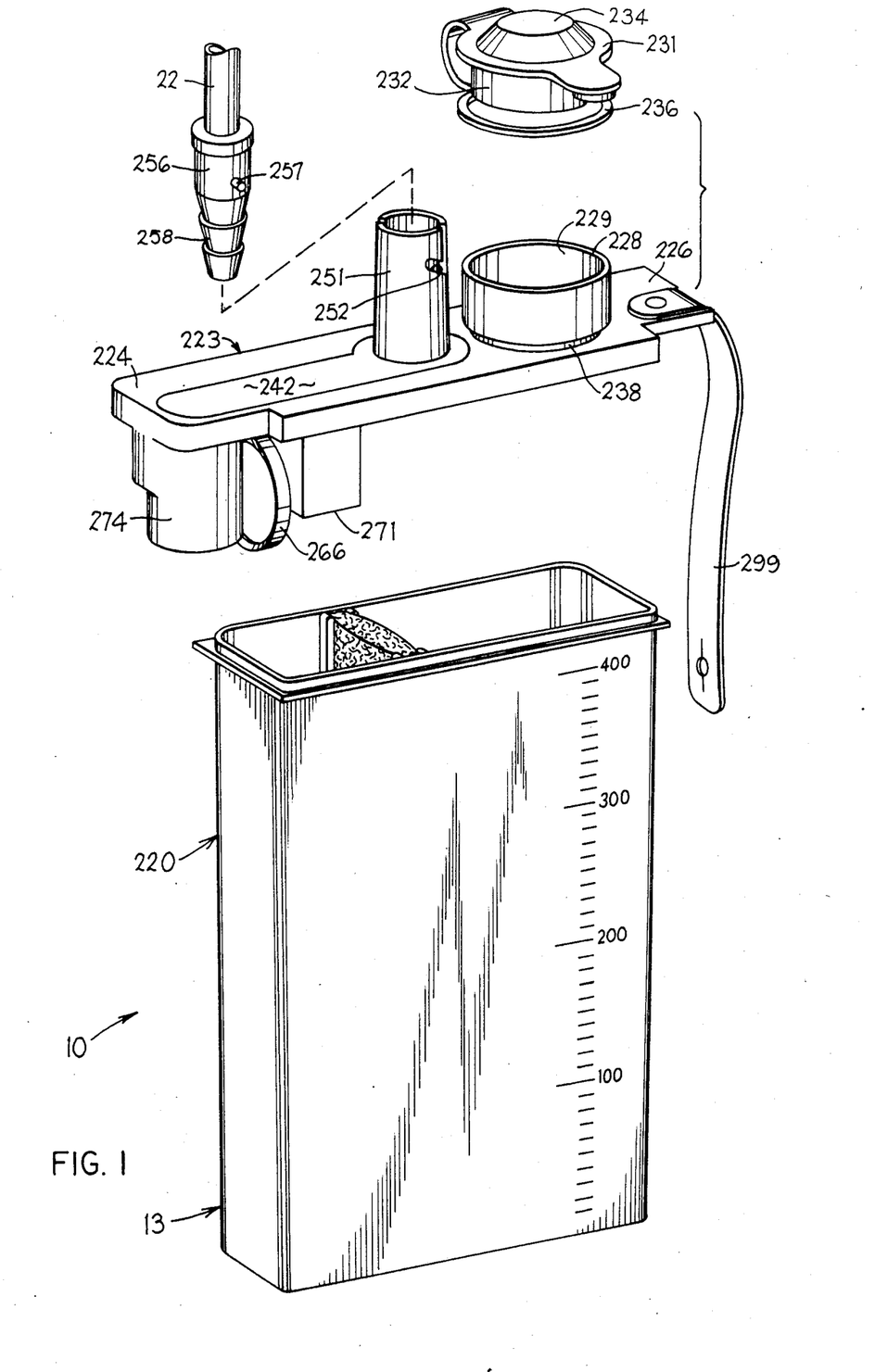
FIG. 1 is an exploded pictorial view of a drain reservoir embodying the invention.
Figure 2:
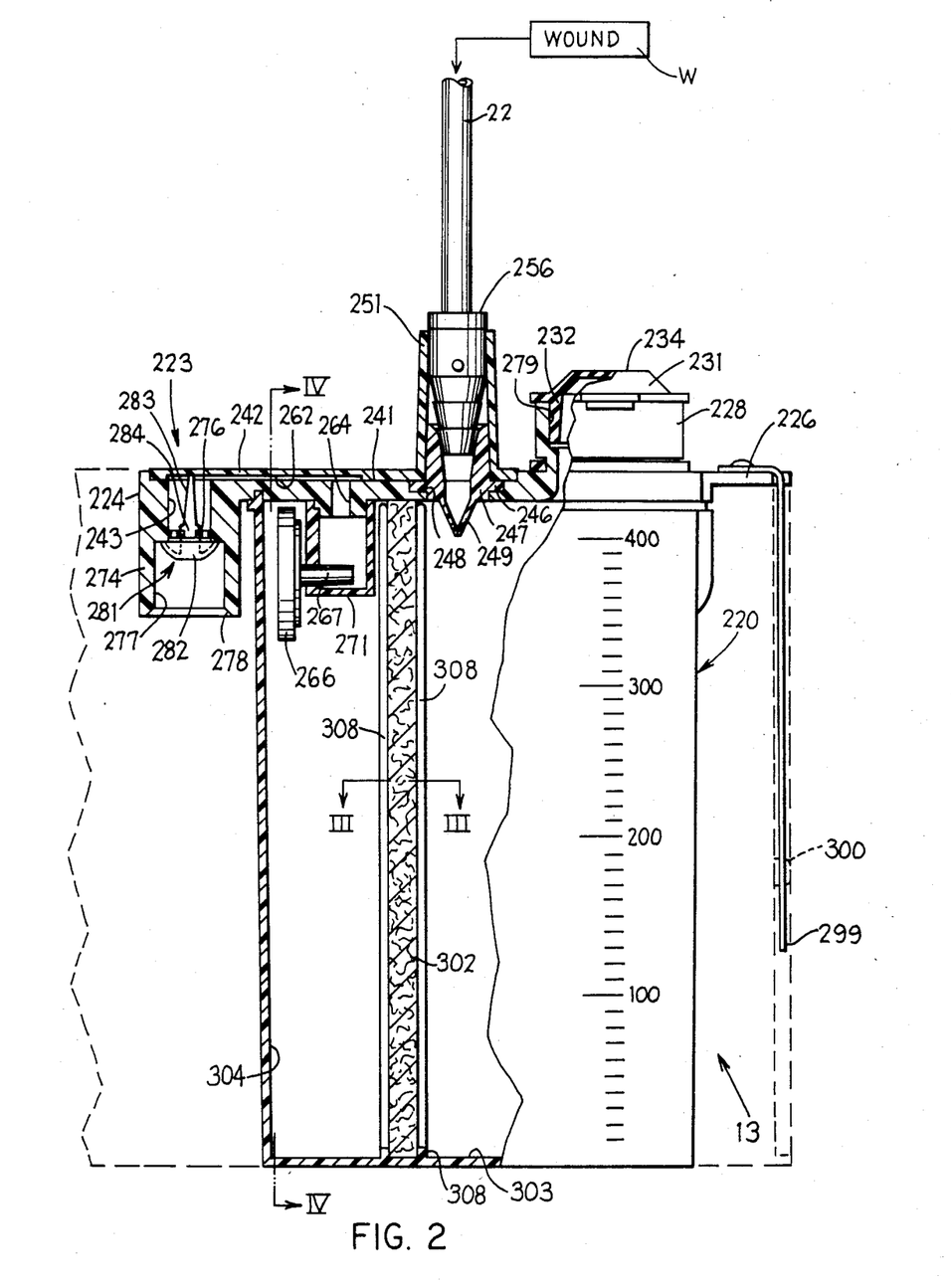
FIG. 2 is a partially broken front view of the drain reservoir of FIG. 1.
Figure 3:
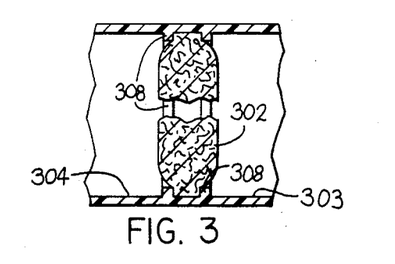
FIG. 3 is an enlarged fragmentary cross-sectional view taken substantially on the line III—III of FIG. 2.

A continuous vacuum drainage system 10, for draining a closed wound, includes a base unit 12 (FIG. 6) and a drain reservoir 13 (FIGS. 1 and 2). The drain reservoir is releasably securable to the base unit for partial evacuation to a subatmospheric (negative) pressure. A wound drain tube 22 is used to connect the reservoir 13 to a patient's wound W to be vacuum drained. The reservoir 13 is disconnectable from the base unit 12 without impairing the negative pressure within the reservoir 13. Thus, the reservoir 13 can be used for vacuum wound drainage both while connected to the base unit 12, as well as after disconnection from the base unit, thus permitting the reservoir to be carried by the patient or on a mobile patient support (not shown) to locations remote from the base unit 12.

Figure 6:
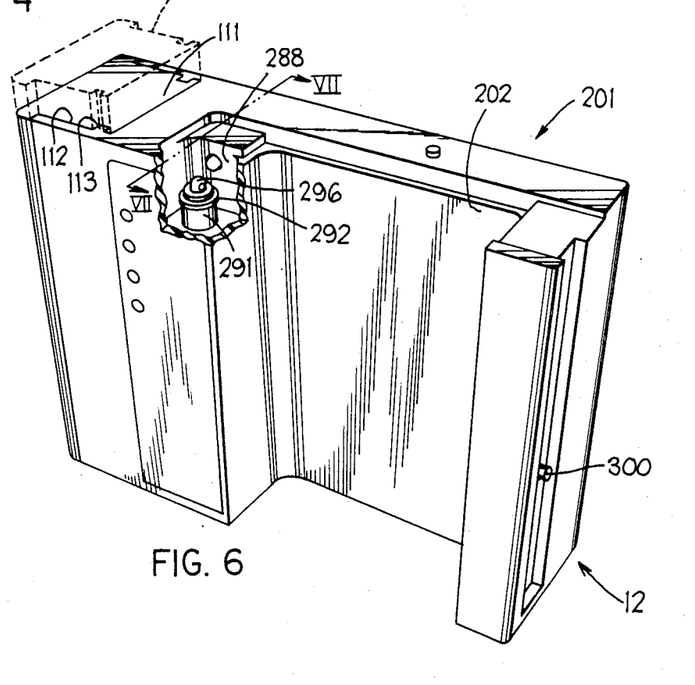
FIG. 6 is a pictorial, partially broken view of a base unit for receiving the drain reservoir of FIG. 1.
Figure 7:
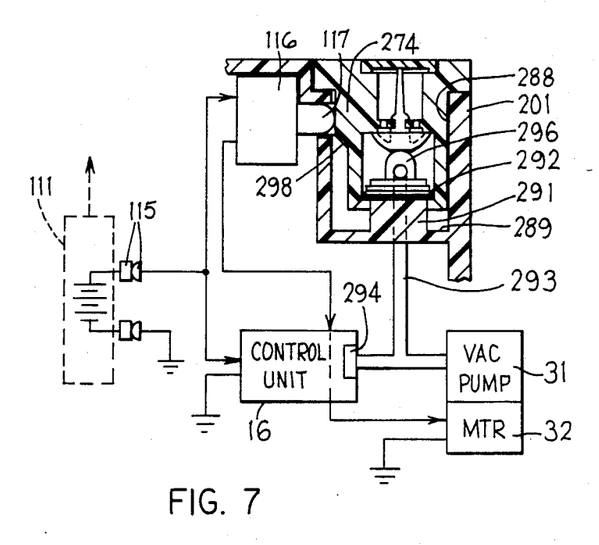
FIG. 7 is a fragmentary cross-sectional view substantially taken on the line VII—VII of FIG. 6.

The base unit 12, in the embodiment shown in FIGS. 6 and 7, comprises a housing 201 having a forwardly facing groove 202 into which the reservoir 13 is downwardly insertable. As schematically indicated in FIG. 7, the housing 201 contains a control unit 16, which may be of the type shown in prior U.S. application Ser. No. 404,791 assigned to the assignee of the present invention, which control unit 16 is enabled by actuation of a power switch 116 to energize the motor 32 of a vacuum pump 31 from an electric power source such as a battery pack 111. The mentioned elements 16, 31, 32, 111 and 116 preferably operate substantially in the manner described in aforementioned application Ser. No. 404,791, such that with the actuator 117 of switch 116 actuated by insertion of a receptacle 113 into the recess 202 in the housing 201 of the base unit 12, the control unit 16 will sense the level of vacuum in the drain reservoir 13 (means of a conventional vacuum transducer 294) and, if an insufficient vacuum level exists, will cause the pump 31 to run for a sufficient time as to reduce the pressure in the drain reservoir 13 to a desired subatmospheric level.

In the embodiment shown, the battery pack 111 is arranged as a unit vertically slidable into and removable from a recess 112 in the left (FIG. 6) end of the housing 201 in which it is vertically guided by tongue-in-groove means 113. As schematically indicated in FIG. 7, electrical contact between the battery pack 111 and electrical apparatus within the housing 201, including switch 116 and control unit 16, is established, with the battery pack 111 installed in the housing as indicated in solid lines in FIG. 6, by means of opposed relatively vertically movable conductive contacts 115.

The drain reservoir 13 (FIGS. 1 and 2) comprises a hollow, substantially rectangular, upward opening bottle 220, the top of which is closed by a fixed cover 223. The left and right ends 224 and 226 of the cover 223 overhang the sides of the bottle 220. An emptying spout 228 fixedly upstands from the cover 223 above the rightward portion of the bottle 220 and has a through opening 229 for emptying liquid from the bottle. A resilient cap 231 is positionable atop the spout 228 and has a skirt 232 snugly received in the through opening 229 for sealing the spout against air leakage therepast into the bottle 220. In the embodiment shown, the top 234 of the cap 231 resiliently flexes to a concave shape, when the bottle is at a subatmospheric pressure, to visually indicate that a subatmospheric pressure condition exists in the bottle. A retaining ring 236 fixed to the cap 231 fits in an undercut 238 in the spout 228 to prevent loss of the cap 231 when it is removed from the spout for pouring liquid from the bottle.

An upward opening recess 241 extends from the central portion of cover 223 nearly to the left end thereof. A platelike closure 242 is sealingly fixed in the recess 241 to hold the radially protruding flange 246 of a tubular resilient valve member 247 in a subrecess 248 of the cover 223. At the lower end of the tubular valve member 247 is a one-way, or check, valve, here of the so-called "duck bill" type, which permits fluid flow into, but not out of, the bottle 220. The platelike closure 242 has an upstanding chimney 251 closely surrounding the tubular valve member 247 and extending upward therebeyond. The chimney 251 has diametrally opposed, substantially J-shaped, bayonet locking slots 252. The resilient member 247 and chimney 251 form a socket compatible with a conventional connector plug 256 on the outlet end of the wound drain tube 22. The connector plug 256 has diametrally extending bayonet pins 257 coactive with the J-shaped locking slots 252 to releasably hold the plug 256 in the chimney 251 with the tapered, frustoconically ridged bottom 258 of the plug snugly fitted in sealed relation in the upper portion of the tubular valve member 247 in spaced relation above the duck bill valve 249.

A vacuum passage is formed by a leftwardly-rightwardly extending recess 262 in the underside of the platelike closure 242 to the left of the chimney 251 and vertical holes 263 and 264 extending downward from the ends of such recess 262 in the overhanging left end portion 224 of the cover 223 and in the portion of the cover 223 in the leftward portion of the bottle 220.

Figure 4:
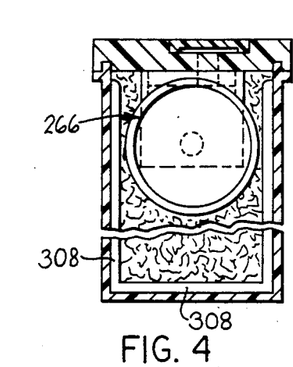
FIG. 4 is a fragmental sectional view substantially taken on the line IV—IV of FIG. 2.
Figure 5:
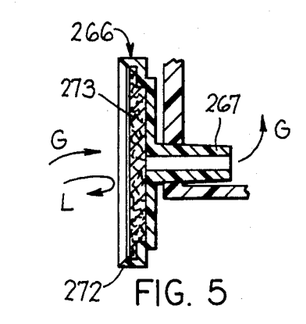
FIG. 5 is a central cross-sectional view substantially taken on the line V—V of the hydrophobic filter unit of FIG. 4.

A commercially available, dishlike, microporous hydrophobic filter unit 266 (FIGS. 2, 4 and 5) is disposed in the upper leftward portion of the bottle 220 and has a rightwardly protruding hollow outlet stem 267 communicating, here through a hollow adapter 271, with the hole 264. In the embodiment shown, the microporous hydrophobic filter unit 266 comprises a disklike, undercut surround 272 from which said stem 267 extends and which contains a 0.2 micron polytetrafluoroethylene (PTFE, or as known by the mark Teflon) screen 273, comprising material known as Goretex 111177, backed by polypropylene, which filter unit is available from Filtertek, Inc. of Hebron, Ill. The hydrophobic filter unit 266 is capable of passing gases therethrough (as indicated by the arrows G in FIG. 5) but not liquid (as indicated by the arrow L).

At the left end of the vacuum passage (formed by recess 262 and holes 263 and 264 FIG. 2), the hole 263 extends part way down into a leg 274 integrally depending from the left end of the cover 226, near the left side of the bottle 220. Approximately midway down the leg 274, a wall 276 extends diametrally and forms a bottom to the hole 263, separating same for a larger diameter downwardly opening recess 277 terminating at its lower end in a vacuum port 278.

A check, or one-way, valve 281 here comprises a resilient umbrella valve head 282 from which a resilient coaxial stem 283 extends upward through a central opening in the wall 276, the stem being enlarged adjacent its lower end at 284 immediately above the wall 276 to firmly hold the radially enlarged head 282 in sealing contact against the upper end wall of the recess 277. Holes through the peripheral portion of the wall 276 are thus normally closed by the umbrella valve head 282 which radially overlaps same when the air pressure in the recess 277 is higher than that in the hole 263, i.e., when there is a subatmospheric pressure in the bottle 220. On the other hand, the valve head 282 is capable of deflecting downward at its periphery in response to a drop in pressure in the recess 277 to below the pressure in the bottle 220, so as to draw air from the bottle through the hydrophobic filter 266, passage 264, 262, 263 and then down through the recess 277.

In the embodiment shown, the base unit housing 201 has a recess 288 (FIGS. 6 and 7) which opens upward immediately to the left of the bottle receiving groove 202. The recess 288 is sized to receive downward thereinto, in clearance relation, the depending leg 274 of the bottle cover 223. Projecting upward through the floor 289 of the recess 288 is a hollow cylindrical fitting 291 on which is coaxially fixed a resilient annular seal 292. The fitting 291 is hollow and connected to the vacuum pump 31 by a vacuum line 293 which also connects to a conventional vacuum transducer 294 in the control unit 16, so that the control unit 16 can be influenced by the level of subatmospheric pressure in the line 293. The fitting 291 has a perforated head 296.

With the bottle 220 received in the forward opening groove 202 and the depending leg 274 downwardly received in the recess 288 as in FIG. 7, the vacuum port 278 is sealed by the annular seal 292 to effect an air-tight vacuum connection between the vacuum pump 31 and the recess 277 in the drain reservoir cover 223. Operation of the vacuum pump 231 reduces the gas pressure in the recess 277 and when the latter is at a level below the gas pressure within the bottle 220, the periphery of the umbrella valve head 282 is pulled downward by such pressure differential to open communication between the recess 277 and the passage 263, 262, 264 and hence through the hydrophobic filter 266 to the interior of the bottle 220 to lower the pressure in the bottle to a desired subatmospheric pressure. Such connection of the vacuum pump 31 to the bottle 220 is normally carried out after the tube 22 has been emplaced in a closed wound W.

In the embodiment shown in FIGS. 6 and 7, the vacuum pump 31 is enabled by depression of the switch actuator 117 by contact with the side of the leg 274 as the drain receptacle 13 is being downwardly received in the base unit 12 (with bottle 220 in forward facing groove 202 and leg 274 received in the upward opening recess 288). In the preferred embodiment shown, the switch actuator 117 also acts as a mechanical aid to help prevent unintended movement of the drain receptacle 13 out of its vacuum charging position in the base unit 12 shown in FIG. 7. Indeed, in one embodiment, the side of the leg 274 had a shallow depression receiving the switch actuator button 117 with the drain reservoir 13 firmly pushed down in its vacuum charging position in the recesses 202 and 288 of the base unit 12. However, in the preferred embodiment shown in FIGS. 2, 6 and 7, the actuator 117 is depressed by a ramp 298 on the side of the leg 274 during insertion of the drain reservoir 13 in the base unit 12 and then simply bears frictionally on the leg 274, and a strap 299 fixedly depending from the right side of the cover 223 (FIGS. 1 and 2) buttons onto a pin 300 projecting from the right side of the base unit 12 (FIGS. 2 and 6) to help hold the bottom of the leg 274 firmly and sealingly against the annular vacuum seal member 292, so as to seal the vacuum port 278. In this way, with the tube 22 inserted in a closed wound W, the bottle 220 is evacuable to a subatmospheric pressure by means of the vacuum pump 31.

The drain reservoir 13 can be left in place in the base unit 12 in its FIG. 7 position. Alternatively, the thus "vacuum charged" drain reservoir can be forced upward with respect to the base unit 12 to unseat the switch actuator 117 from the detent 298 and thus permit the drain reservoir 13 to be lifted out of contact with the base unit 12. Thereafter, the drain reservoir 13, connected to the patient by means of the drain tube 22, can continue to draw drainage liquid from the wound W, and indeed can be moved with the patient to a location remote from the base unit 12, in the same general manner as in abovementioned U.S. application Ser. No. 404,791.

During evacuation of the drain reservoir 13 by the base unit 12, the hydrophobic filter unit 266 blocks movement of any liquid in the bottle 220 therepast into the hollow adapter 271, passage 262–264 and base unit 12. Similarly, with the drain reservoir 13 disconnected from the base unit 12, the hydrophobic filter 266 protects against entry of liquid from the bottle 220 therepast into the adapter 271 and passage 262–264 (to thereby prevent contamination of the vacuum pump system in the base unit 12 upon latter connection of the drain reservoir 13 to the base unit 12 for recharging the vacuum bottle 220). Thus, the hydrophobic filter unit 266 avoids the need for any sort of tilt responsive or fill responsive valve to close the passage 262–264 against drainage liquid. The hydrophobic filter unit 266 at any time permits removal of gases from the drain reservoir 13 by the base unit 12 to restore subatmospheric pressure in the bottle 220 (assuming that the bottle 220 is not filled with liquid), since the hydrophobic filter unit 266 will pass gases therethrough but not liquids.

The drain reservoir 13 installed on the base unit 12 is normally in its upright position shown in FIG. 2. However, when the drain reservoir 13 is separated from the base unit 12, it may be tipped or jiggled or otherwise moved to cause liquid within the bottle 220 to splash onto the surface of the hydrophobic filter unit 266.

To protect the hydrophobic filter 266 against coating with, and hence clogging by, lipids (the fat constituent in the body fluid being collected) a perforate baffle 302 of a nonpolar material is fixed in and extends across the interior of the bottle 220 to divide same into two separate chambers 303 and 304 (FIG. 2) at a location between the wound liquid inlet valve 249 and the hydrophobic filter 266. More particularly, the wound drain tube 22 and the emptying spout 228 communicate with the chamber 303 and the hydrophobic filter unit 266 communicates with the chamber 304.

In the embodiment shown, the baffle 302 is formed as a substantially rectangular panel extending the full height and thickness of the interior of the bottle 220. The baffle 302 can be of any convenient thickness but in the particular embodiment shown is in the range of $\frac{1}{4}$ to $\frac{3}{8}$ inch thick, for example $\frac{1}{2}$ inch thick. To maximize the area of the nonpolar material available for contact with fatty substances in the liquid within the bottle 220, the baffle 302 is preferably constructed of fibers randomly arranged in overlapping fashion, namely to form a fibrous mat wherein the fibers are held in place with respect to each other by a minimal amount of synthetic resin, preferably a nonpolar resin. Examples of suitable nonpolar materials include polypropylene, polyethylene and polystyrene. The resulting padlike baffle 302 is substantially shape-retaining and self-supporting. In the embodiment shown, baffle 302 is flexible enough to be bent or curved manually, but not sufficiently flexible as to be distorted by passage of wound drainage liquids therethrough in normal use.

It is contemplated that the baffle 302 may be otherwise made perforate to allow flow therethrough of wound drainage liquids and to have a high surface area for maximum attraction of lipids thereto, but the fibrous mat embodying the invention provides a low cost, readily available, and particularly effective form of perforate, high surface area baffle. One successful form of fibrous mat material for the baffle 302 is readily commercially available from Minnesota Mining and Manufacturing (3M) of Minneapolis, Minn. under the name "Superpolish Polyester" and marketed as manual polishing or scrubbing pads for household and industrial use.

Since polyester, polypropylene and polystyrene are successively more nonpolar, it is contemplated that a polypropylene and polystyrene baffle 302 may be even more effective than such polyester baffle.

The baffle 302 does not operate as a mechanical filter, that is, it does not operate by providing pores of a size to exclude large particles and pass small particles, Indeed, some of the components in the wound drainage liquid intended to be blocked by the baffle 302, namely lipids, may be physically smaller than other components, such as red blood cells, which need not be stopped by the baffle 302. Instead, the nonpolar material of the baffle 302 attracts lipids in the wound drainage liquid, since such lipids are nonpolar substances, so as to be attracted to other nonpolar substances.

The baffle 302 contains many through passages of small diameter, relatively great length and tortuous configuration. Thus, lipids attempting to pass through the baffle are forced to remain close to the surface of the nonpolar material of the baffle for a relatively long time to thereby increase the probability of being attracted to and trapped on the surface of the nonpolar material of the baffle. Also, maximizing the surface area of material exposed to the wound drainage liquid further maximizes the opportunity for lipids to be attracted to the material surface of the baffle. Accordingly, various components of the wound drainage liquid pass freely through the thickness of the baffle 302, namely the polar components therein which are not attracted by the nonpolar material of the baffle, while the nonpolar components of the liquid, namely lipids, tend to be entrapped by and stick to the material of the baffle.

In this way, the hydrophobic filter is protected by the baffle 302 against clogging by the lipids and fatty substances in the wound drainage liquid. This permits the use of a hydrophobic filter 266 which is particularly subject to clogging by the nonpolar components (lipids) of the wound drainage liquid, here for example a hydrophobic filter of PTFE material, which is also a nonpolar substance and hence attractive to lipids in the wound drainage liquid.

In the particular embodiment shown, the baffle 302 is held fixedly in position in the bottle 220 by ridges 308 molded into the inner surfaces of the front and rear walls and bottom wall of the bottle. The baffle 302 can be installed by sliding same down into the bottle 220 with its edges between the ridges 308 prior to installation of the cover 223 fixedly thereon.

OPERATION

Although the foregoing detailed description makes clear the operation of the device, such operation is summarized below for convenient reference.

With the remote end of the wound drainage tube 22 inserted in a closed wound W, as part of a surgical operation, and the drain receptacle 13 inserted down into the base unit 12, the switch member 117 and strap 298 hold the vacuum port 278 of the drain receptacle snugly against the seal 292 of the base unit 12 with the perforated head 296 in the recess 277 beneath the one-way valve 281. Engagement of the switch actuator 117 by the detent 298 compresses the switch actuator 117, turning on the switch 116 and enabling the control 16. Thus, when the vacuum transducer 294 in control unit 16 senses that the pressure in the bottle 220 is above a desired subatmospheric pressure range, for example at atmospheric pressure, it energizes the motor 32 of the vacuum pump 31 so that the vacuum pump 31 starts and lowers the pressure at the perforated head 296 and in the recess 277 of the drain reservoir 13. This reduced pressure opens the valve 281 to permit the vacuum pump to draw gases through the passage 262–264, the adapter 271 and the hydrophobic filter 266 from the interior of the bottle 220. The action of the control unit 16 may be like that described in abovementioned U.S. application Ser. No. 404,791.

The resulting subatmospheric pressure in the interior of the bottle 220, contrasted with the atmospheric pressure in the closed wound W, causes the drainage liquid from the wound W to flow through the drain line 22 and one-way valve 249 into the chamber 303 of the bottle 220.

The liquid drawn from the wound W will normally include blood as well as other material, such as lipids, released by surgical contact with tissue and bone. The wound drainage fluid can be considered as comprising blood as a solution with suspensions. The lipids are one of the components suspended in the blood. The blood is approximately 75% water. Water is a polar substance and thus one could say that the general characteristic of blood is that it is polar. In general, the solids in blood are polar because they are dissolvable in water with the polar components tending to be dissolvable in water. Nonpolar materials characteristically are not dissolvable in water. The baffle 302, as above stated, is nonpolar. The nonpolar components in the wound drainage liquid, before thay can reach the hydrophobic filter 266, must come into contact with the material of the baffle 302. The nonpolar baffle material attracts the nonpolar material in the wound drainage liquid, namely the lipids. Thus, the nonpolar material in the wound drainage liquid, namely the lipids, are thus captured by the material of the baffle 302. Thus, the mainly polar components of the wound drainage liquid, which are free to pass through the baffle 302, are the only components which thus can enter the chamber 304, the lipids being excluded. Accordingly, the hydrophobic filter 266 may be contacted by liquids in the chamber 304, upon tilting or jiggling of the drain reservoir, or upon substantial filling thereof, but is protected from contact with nonpolar materials, particularly lipids. Thus, while the hydrophobic filter 266 may become wetted from time to time, it does not become coated and clogged. Hence, the hydrophobic filter tends to stay operative for its intended purpose of allowing evacuation of gas from the bottle 220 via vacuum pump 31 but preventing liquid flow therepast as would contaminate or disable the vacuum pump 31.

Were the hydrophobic filter 266 to become coated with a sufficient amount of fatty substance collected from the wound in the patient, the sensor 294 in the control unit 16 would thus shut off the vacuum pump 31 in the belief that an excessive vacuum existed in the drain reservoir 13, even if an insufficient vacuum existed in the drain reservoir. The drain reservoir 13 would therefore no longer properly vacuum drain the wound W and the system would be at that time nonoperative.

Depending on the character of the surgical operation and the lipid content in the drained liquid, and the agitation of the drain receptacle, if any, leading to coating of the hydrophobic filter 266, coating of the hydrophobic filter to the point of inoperativeness might occur in just a few hours (for example two or three hours). On the other hand, a given drain reservoir 13 may be required to drain a wound in a patient for, typically, 24 to 72 hours. Hence, in the absence of the baffle 302, the drain reservoir 13 may require, under certain circumstances, premature replacement. The baffle 302, on the other hand, has enabled use of a drain reservoir 13 and periodic recharging thereof with vacuum by a base unit 12 for the 24 to 72 hour periods typically required for patient support.

Once the drain reservoir 13 has been charged with vacuum by the base unit 12, and removed from the base unit, to allow more freedom in placement with respect to the patient and to allow movement of the patient, the subatmospheric pressure in the bottle 220 is maintained by the closed resilient cap 231 (which by being indented in its center indicates the presence of subatmospheric pressure in the bottle 220), and the closed umbrella valve 281.

Normally the drain receptacle 13 will be removed from the base unit 12 after the vacuum pump 31 has completed its lowering of the interior of the bottle 220 to subatmospheric pressure in the desired range and such vacuum pump 31 is turned off. Indeed, lifting of the drain receptacle 13 upward out of its engagement with the base unit 12 will shut off the vacuum pump 31 by deactuating the switch actuator 117, by in turn moving out of contact therewith the depending portion 274 of the drain reservoir 13.

The bottle 220 may eventually become filled, in which case the cap 231 is removed from the spout and liquid is poured out of the drain reservoir by tilting the bottle 220. Once that is done, the pressure is atmospheric in the bottle. Similarly, the bottle 220 may become partially filled with wound drainage liquid and at some time the pressure therein may approach atmospheric pressure whereupon the top pressure 234 of the cap 231 pops up to indicate that charging of the drain reservoir with vacuum is required. Under either condition, the drain reservoir may be engaged with a conveniently located base unit 12 for recharging with subatmospheric pressure in the manner above described.

Once the drain reservoir 13 has performed its wound draining function, the drain tube 22 can be discarded but the base unit 12 can be used again for another patient and with other drain receptacles, without danger of contamination, because the hydrophobic filter 266 has prevented liquid in the drain reservoir 13 from reaching the base unit 12.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A continuous vacuum wound drainage system, comprising:
   a drain reservoir capable of being evacuated to a subatmospheric pressure;
   wound connection means for connecting said drain reservoir to a wound and therewith for vacuum draining fluids from the wound;
   vacuum source connecting means for connecting said drain reservoir to a vacuum source and therewith for providing the subatmospheric pressure in said drain reservoir;
   hydrophobic filter means permitting gas flow therethrough but blocking flow of liquid therethrough from said drain reservoir to said vacuum source connecting means for attaining the subatmospheric pressure in a reservoir by said vacuum source while avoiding contamination of a vacuum source by liquid from said drain reservoir;
   baffle means constructed for preventing fatty substances from flowing therethrough, said wound connecting means and said hydrophobic filter means communicating with respective first and second spaces within said drain reservoir, said baffle means defining said first and second spaces.

2. The apparatus of claim 1 in which said baffle means comprise a member having nonpolar surface characteristics for nonpolar attraction of fatty substances from a flow therepast but open to a flow of dissimilar wound drainage fluids.

3. The apparatus of claim 2 in which said member is made of a synthetic nonpolar material.

4. The apparatus of claim 1 in which said drain reservoir comprises a bottle with a cup-shaped upward opening configuration closed by a top cover, said cover having one end overhanging said bottle, said vacuum source connecting means including a vacuum port in a overhanging end connectable to said vacuum source, a vacuum passage extending from said vacuum port inboard from said overhanging end and opening to the interior of said bottle through said hydrophobic filter means, said hydrophobic filter means being located under said cover and facing into the interior of said bottle.

5. The apparatus of claim 4 in which said wound connecting means includes means on said cover located away from said vacuum connecting means and communicating through said cover with said bottle interior, an emptying spout on said cover and communicating with said bottle interior, a cap locatable on said spout for closing same against air leakage into said bottle and removable therefrom to allow emptying of liquid from said bottle through said spout.

6. The apparatus of claim 5 in which said cap is resilient and has a portion distortable by a pressure drop thereacross to indicate a subatmospheric pressure in said bottle.

7. A continuous vacuum wound drainage system, comprising:
   a drain reservoir capable of being evacuated to a subatmospheric pressure;
   wound connection means for connecting said drain reservoir to a wound and therewith for vacuum draining fluids from the wound;
   vacuum source connecting means for connecting said drain reservoir to a vacuum source and therewith for providing the subatmospheric pressure in said drain reservoir;
   liquid blocking means blocking flow of liquid from said drain reservoir to said vacuum source connecting means, to thereby avoid contamination of a vacuum source by liquid from said drain reservoir;
   baffle means constructed for preventing fatty substances from flowing therethrough, said wound connecting means and said liquid blocking means communicating with respective first and second spaces within said drain reservoir, said baffle means defining said first and second spaces, in which said baffle means comprise a member having nonpolar surface characteristics for interfering with flow of fatty substances therepast but open to a flow of dissimilar wound drainage fluids, and in which said member comprises a mat of fibrous nonpolar material presenting relatively high surface area of material to flow of lipids so as to maximize attraction of lipids to said member from said flow, said fibrous mat having fibers held together in matted relation by a binding material.

8. A continuous vacuum wound drainage system, comprising:
   a drain reservoir capable of being evacuated to a subatmospheric pressure;
   wound connection means for connecting said drain reservoir to a wound and therewith for vacuum draining fluids from the wound;
   vacuum source connecting means for connecting said drain reservoir to a vacuum source and therewith for providing the subatmospheric pressure in said drain reservoir;
   liquid blocking means blocking flow of liquid from said drain reservoir to said vacuum source connecting means, to thereby avoid contamination of a vacuum source by liquid from said drain reservoir;
   baffle means constructed for preventing fatty substances from flowing therethrough, said wound connection means and said liquid blocking means communicating with respective first and second spaces within said drain reservoir, said liquid blocking means defining said first and second spaces, in which said baffle means comprises a baffle fixedly dividing said drain reservoir into separate first and second chambers respectively defining said first and second spaces in which respectively lie said wound connecting means and said vacuum source connecting means, said baffle being a generally self-supporting mat of nonpolar synthetic material.

9. The apparatus of claim 8 in which said drain reservoir comprises a hollow bottle with a wall enclosing an interior space, means on said wall for locating said baffle fixedly to divide said interior space into said first and second chambers.

10. The apparatus of claim 9 in which said wound connecting means comprises a wound drain port in said bottle wall in said first chamber, the bottle wall in said first chamber including a bottle emptying port for emptying said bottle of liquid, said vacuum source connecting means comprising a vacuum port at which vacuum source is connectable, said liquid blocking means separating said second chamber from said vacuum port, said liquid blocking means comprising a hydrophobic filter capable of permitting withdrawal of gases but not liquid from bottle by a said vacuum source.

11. A continuous vacuum wound drainage system, comprising:
- a drain reservoir capable of being evacuated to a subatmospheric pressure;
- wound connection means for connecting said drain reservoir to a wound and therewith for vacuum draining fluids from the wound;
- vacuum source connecting means for connecting said drain reservoir to a vacuum source and therewith for providing the subatmospheric pressure in said drain reservoir;
- liquid blocking means blocking flow of liquid from said drain reservoir to said vacuum source connecting means, to thereby avoid contamination of a vacuum source by liquid from said drain reservoir;
- baffle means constructed for preventing fatty substances from flowing therethrough, said wound connecting means and said liquid blocking means communicating with respective first and second spaces within said drain reservoir, said baffle means defining said first and second spaces, in which said liquid blocking means comprises a hydrophobic filter, said vacuum source connecting means having a vacuum port for connection to a vacuum source, said vacuum source connecting means comprising a valve interposed between said hydrophobic filter and said vacuum port, said valve being normally closed to prevent entry of ambient air into said drain reservoir and being openable in response to connection of a vacuum source to said vacuum port.

12. The apparatus of claim 11 including a vacuum source connected to said drain reservoir at said vacuum port, said vacuum source including seal means registering with said vacuum port to seal the connection therebetween against air leakage.

13. The apparatus of claim 12 including a base unit, said vacuum source comprising a vacuum pump housed in said base unit, said base unit including a power source connection for powering said vacuum pump and switch means actuable for powering said vacuum pump from said power source connection.

14. The apparatus of claim 13 in which said switch means has an actuating member actuable by a portion of said drain reservoir upon sliding into position of said drain reservoir onto said base unit in a direction to register said seal means with said vacuum port and effecting of connection of said vacuum source to said vacuum port, said switch actuating member being connected to turn on said vacuum pump to evacuate said drain reservoir, said actuating member and said portion of said drain reservoir also engaging to assist a vacuum seal between said drain reservoir and base unit.

15. A continuous vacuum wound drainage system, comprising:
- a drain reservoir capable of being evacuated to a subatmospheric pressure;
- wound connection means for connecting said drain reservoir to a wound and therewith for vacuum draining fluids from the wound;
- vacuum source connecting means for connecting said drain reservoir to a vacuum source and therewith for providing the subatmospheric pressure in said drain reservoir;
- liquid blocking means blocking flow of liquid from said drain reservoir to a vacuum source connecting means, to thereby avoid contamination of a vacuum source by liquid from said drain reservoir;
- said liquid blocking means comprising a microporous hydrophobic filter mounted on said drain reservoir with one side facing into the interior of said drain reservoir, said vacuum source connecting means comprising a vacuum passage on said drain reservoir extending from the other side of said hydrophobic filter to a vacuum port open outwardly of said drain reservoir, said hydrophobic filter being provided as the sole means preventing overflow of liquid from said interior of said drain reservoir into said vacuum passage;
- selective means comprising a baffle separating said bottle into first and second chambers, said first chamber communicating with said vacuum source connecting means and into which said liquid blocking means faces, said second chamber communicating with said wound connection means, said baffle being porous and of nonpolar material capable of removing fatty materials from fluids passing between said members.

16. Apparatus for selectively blocking passage of fatty substances in a liquid flow path, comprising:
- receiver means having inlet means for receiving a multi-constituent liquid including fatty particles as one constituent thereof and further having outlet means for venting gases from said receiver means, said outlet means having hydrophobic filter means permitting said venting of gases but not of liquid therepast from said receiver means, said filter means comprising a hydrophobic filter blockable against gas flow therethrough by contact with fatty substances in said liquid;
- means for protecting said hydrophobic filter against blocking by fatty substances and comprising a porous a baffle of material attractive to fatty substances and located in said receiver means such that flow from said inlet means must pass therethrough to reach said hydrophobic filter.

17. The apparatus of claim 16 in which said baffle comprises a pad of fibers of nonpolar material in which said fibers are arranged in matted form and are held together by a binder material so that said pad is substantially shape-retaining and self-supporting, said binder material being unaffected by human body fluids.

18. The apparatus of claim 16 in which said baffle comprises a mat of fibers in which the fibrous material is selected from the group consisting of polypropylene, polyethylene and polystyrene.

* * * * *

UNITED STATES PATENT AND TRADEMARK OFFICE
CERTIFICATE OF CORRECTION

PATENT NO. : 4,655,754

DATED : April 7, 1987

INVENTOR(S) : James W. Richmond et al

It is certified that error appears in the above-identified patent and that said Letters Patent is hereby corrected as shown below:

Column 11, Line 4; Change "from bottle by a said vacuum source" to ---from said bottle by a vacuum source---.

Column 12, Lines 47 - 48; Change "a porous a baffle" to ---a porous baffle---.

Signed and Sealed this

Tenth Day of November, 1987

Attest:

DONALD J. QUIGG

*Attesting Officer*   *Commissioner of Patents and Trademarks*